US008029804B2

(12) United States Patent
Ching et al.

(10) Patent No.: US 8,029,804 B2
(45) Date of Patent: Oct. 4, 2011

(54) RECOMBINANT CHIMERIC ANTIGENS FOR DIAGNOSIS AND PREVENTION OF SCRUB TYPHUS

(75) Inventors: Wei-Mei Ching, Bethesda, MD (US); Chien-Chung Chao, N. Potomac, MD (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 12/467,533

(22) Filed: May 18, 2009

(65) Prior Publication Data

US 2009/0285857 A1   Nov. 19, 2009

Related U.S. Application Data

(60) Provisional application No. 61/054,022, filed on May 16, 2008.

(51) Int. Cl.
*A61K 39/02* (2006.01)
(52) U.S. Cl. ............... 424/234.1; 424/269.1; 424/185.1; 424/192.1; 435/7.1; 435/7.2; 435/7.32; 530/350
(58) Field of Classification Search .................. None
See application file for complete search history.

(56) References Cited

U.S. PATENT DOCUMENTS

| 6,482,415 | B1 | 11/2002 | Ching |
| 6,699,674 | B2 | 3/2004 | Ching |
| 7,335,477 | B2 | 2/2008 | Ching |
| 2003/0165523 | A1 | 9/2003 | Ching et al. |

FOREIGN PATENT DOCUMENTS

| WO | WO 02/20611 A1 | 3/2002 |
| WO | 02083069 A2 * | 10/2002 |
| WO | 2003096974 A2 * | 11/2003 |

OTHER PUBLICATIONS

Greenspan et al (Nature Biotechnology 7: 936-937, 1999.*
Chothia et al (The EMBO Journal, 1986, 5/4:823-26).*

* cited by examiner

*Primary Examiner* — Jennifer Graser
(74) *Attorney, Agent, or Firm* — Joseph K. Hemby, Jr.; Albert M. Churilla; Ning Yang

(57) ABSTRACT

Recombinant chimeric antigens comprising unmodified and modified reactive polypeptide fragments of expressed product of the recombinant 56 kDa proteins of multiple strain of scrub typhus, such as Karp, Kato (Ktr56), Gilliam (Gmr56), and TA763 (TAr56). The invention is useful for detecting prior exposure to a number of strains of scrub typhus, based on the strength of reaction toward the chimeric protein and as a component in vaccine formulations and production of immune globulins for passive prophylaxis and immunity in subjects against heterologous infections.

7 Claims, 4 Drawing Sheets

Figure 2A

Full length 56 kDa from Karp strain: variable domain 1 is underlined; variable domain 2 is bolded, variable domain 3 is double underlined and variable domain 4 is underlined by dotted line.

```
MKKIMLIASA MSALSLPFSA SAIELGEEGL ECGPYAKVGV VGGMITGVES ARLDPADAEG
KKHLSLTNGL PFGGTLAAGM TIAPGFRAEI GVMYLTNITA QVEEGKVKAD SVGETKADSV
GGKDAPIRKR FKLTPPQPTI MPISIADRDF GIDIPNIPQQ QAQAAQPQLN DEQRAAARIA
WLKNCAGIDY RVKNPNDPNG PMVINPILLN IPQGNPNPVG NPPQRANPPA GFAIHNHEQW
RHLVVGLAAL SNANKPSASP VKVLSDKITQ IYSDIKPFAD IAGIDVPDTS LPNSASVEQI
QNKMQELNDL LEELRESFDG YLGGNAFANQ IQLNFVMPQQ AQQQGQGQQQ QAQATAQEAV
AAAAVRLLNG NDQIAQLYKD LVKLQRHAGI KKAMEKLAAQ QEEDAKNQGE GDCKQQQGTS
EKSKKGKDKE AEFDLSMIVG QVKLYADVMI TESVSIYAGV GAGLAYTSGK IDNKDIKGHT
GMVASGALGV AINAAEGVYV DIEGSYMYSF SKIEEKYSIN PLMASVSVRY NF
```

Kpr56 sequence
```
M TIAPGFRAEI GVMYLTNITA QVEEGKVKAD SVGETKADSV
GGKDAPIRKR FKLTPPQPTI MPISIADRDF GIDIPNIPQQ QAQAAQPQLN DEQRAAARIA
WLKNCAGIDY RVKNPNDPNG PMVINPILLN IPQGNPNPVG NPPQRANPPA GFAIHNHEQW
RHLVVGLAAL SNANKPSASP VKVLSDKITQ IYSDIKPFAD IAGIDVPDTS LPNSASVEQI
QNKMQELNDL LEELRESFDG YLGGNAFANQ IQLNFVMPQQ AQQQGQGQQQ QAQATAQEAV
AAAAVRLLNG NDQIAQLYKD LVKLQRHAGI KKAMEKLAAQ QEEDAKNQGE GDCKQQQGTS
EKSKKGKDKE AEFDLSMIVG QVKLYADVMI TESVSI
```

Figure 2B

TA763r56 Cloning sequence: variable domain 1 is underlined; variable domain 2 is bolded and variable domain 3 is double underlined.

```
MTITPSIRAE LGVMYLRNIS AEVELGKVKA DSGSKTKADS GGETDAPIRK RFKLTPPQPT
IMPISIADRD FGVDVTNIPQ AQVQPPQQAN DPLVRGVRRI AWLKEYAGID YMVKDPNNPG RMMVNPVLLN
IPQGPPAQNP RAAMQPCNIL DHDHWKHFVV GVTALSNANK PSASPVKILS EKITQIYSDI RPFADIAGID
VPDAGLPNSA TVEQIQNKMQ ELNDVLEELR ESFDGYLGGN AFANQIQLNF VMPQQAQQQG QGQQQQAQAT
AQEAVAAAAV RLLNGNDQIA QLYRDLVKLQ RHAGIKKAME KLAAQQEEDA KNQGEGDCKQ QQGTSEKSKE
GSKKEPEFDL SMIVGQVKLY ADVMITESVS I
```

Full length 56 kDa from TA763 strain is: variable domain 1 is underlined; variable domain 2 is bolded, variable domain 3 is double underlined and variable domain 4 is underlined by dotted line.

```
MKKIMLIASA MSALSLPFSA SAIELGDEGG LECGPYAKVG VIGGMITGVE SARLDPTDSE GKKHLSLTTG
MPFGGTLAAG MTITPSIRAE LGVMYLRNIS AEVELGKVKA DSGSKTKADS GGETDAPIRK RFKLTPPQPT
IMPISIADRD FGVDVTNIPQ AQVQPPQQAN DPLVRGVRRI AWLKEYAGID YMVKDPNNPG RMMVNPVLLN
IPQGPPAQNP RAAMQPCNIL DHDHWKHFVV GVTALSNANK PSASPVKILS EKITQIYSDI RPFADIAGID
VPDAGLPNSA TVEQIQNKMQ ELNDVLEELR ESFDGYLGGN AFANQIQLNF VMPQQAQQQG QGQQQQAQAT
AQEAVAAAAV RLLNGNDQIA QLYRDLVKLQ RHAGIKKAME KLAAQQEEDA KNQGEGDCKQ QQGTSEKSKE
GSKKEPEFDL SMIVGQVKLY ADVMITESVS IYAGVGAGLA YTSGKIDDKD TKHTGMVVSG ALGVAINAAE
GVYVDIEGSY MYSFSKIEEK YSINPLMASV GVRYNF
```

Figure 3A Chimeric 1 sequence: modifications of the original variable domains are in bold.

```
MTITPSFRAE  LGVMYLRNIT  AQVEEGKVKA  DSGSKTKADS  GGETDAPIRK
RFKLTPPQPT  IMPISIADRD  FGIDIPNIPQ  QQAQAAQPQL  NDEQRAAARI
AWLKNCAGID  YRVKNPNDPN  GPMVINPILL  NIPQGNPNPV  GNPPQRANPP
AGFAIHNHEQ  WRHLVVGLAA  LSNANKPSAS  PVKVLSDKIT  QIYSDIKPFA
DIAGIDVPDT  SLPNSASVEQ  IQNKMQELND  LLEELRESFD  GYLGGNAFAN
QIQLNFVMPQ  QAQQQGQGQQ  QQAQATAQEA  VAAAAVRLLN  GNDQIAQLYK
DLVKLQRHAG  IKKAMEKLAA  QQEEDAKNQG  EGDCKQQQGT  SEKSKKGKDK
EAEFDLSMIV  GQVKLYADVM  ITESVSI
```

Figure 3B Chimeric 2 sequence: modifications of the original variable domains are in bold.

```
MTITPSIRAE  LGVMYLRNIS  AEVELGKVKA  DSGSKTKADS  GGETDAPIRK
RFKLTPPQPT  IMPISIADRD  FGVDVTNIPQ  AQVQPPQQAN  DPLVRGVRRI
AWLKECAGID  YMVKDPNNPN  GPMMINPILL  NIPQGNPNAQ  GNPPQRANPP
AGFNIHNHEQ  WRHFVVGLAA  LSNANKPSAS  PVKVLSDKIT  QIYSDIKPFA
DIAGIDVPDT  SLPNSASVEQ  IQNKMQELND  LLEELRESFD  GYLGGNAFAN
QIQLNFVMPQ  QAQQQGQGQQ  QQAQATAQEA  VAAAAVRLLN  GNDQIAQLYK
DLVKLQRHAG  IKKAMEKLAA  QQEEDAKNQG  EGDCKQQQGT  SEKSKEGSKK
EPEFDLSMIV  GQVKLYADVM  ITESVSI
```

Figure 3C Chimeric 3 sequence: modifications of the original variable domains are in bold.

```
MTITPSFRAE  LGVMYLRNIT  AQVEEGKVKA  DSGSKTKADS  GGETDAPIRK
RFKLTPPQPT  IMPISIADRD  FGVDVPNIPQ  AQVQPPQQAN  DPLQRGVRRI
AWLKNCAGID  YMVKDPNDPN  GPMMINPILL  NIPQGNPNAQ  GNPPQRANPP
AGFNIHNHEQ  WRHFVVGLAA  LSNANKPSAS  PVKVLSDKIT  QIYSDIKPFA
DIAGIDVPDT  SLPNSASVEQ  IQNKMQELND  LLEELRESFD  GYLGGNAFAN
QIQLNFVMPQ  QAQQQGQGQQ  QQAQATAQEA  VAAAAVRLLN  GNDQIAQLYK
DLVKLQRHAG  IKKAMEKLAA  QQEEDAKNQG  EGDCKQQQGT  SEKSKKGKDK
EAEFDLSMIV  GQVKLYADVM  ITESVSI
```

RECOMBINANT CHIMERIC ANTIGENS FOR DIAGNOSIS AND PREVENTION OF SCRUB TYPHUS

CROSS-REFERENCE TO RELATED APPLICATION

This application claims priority to U.S. provisional application No. 61/054,022 filed May 16, 2008. The contents herein are incorporated by reference.

TECHNICAL FIELD

This invention relates to recombinant chimeric antigens comprising reactive polypeptide fragments of the 56 kDa protein from more than one strain of *Orientia tsutsugamushi* and a method for detecting scrub typhus via serodiagnostic assays using these chimeric antigens. This invention also relates to using chimeric antigens in the production of vaccines, passive prophylactic, and therapeutic agents. The products produced in accordance with this invention may be combined with other pharmaceutically-acceptable bioactive substances.

BACKGROUND ART

Scrub typhus, also referred to as chigger-borne rickettsiosis, mite-borne typhus, Japanese river fever, tropical or rural typhus or tsutsugamushi disease is an acute, febrile disease caused by infection with *Orientia* (formerly *Rickettsia*) *tsutsugamushi*. It accounts for up to 23% of all febrile episodes in endemic areas of the Asia-Pacific region (1). The disease is characterized by a rise in body temperature, skin rash, and severe headaches. This disease may affect the nervous system, with clinical manifestations such as delirium, stupor and muscle fibrillation. The death rate varies from 1 to 30% depending on the virulence of the infecting strain.

Scrub typhus is particularly prevalent in South-East Asia, Korea, Australia, China, Japan, and India. The incidence of disease has increased in some countries during the past several years (40). The causative organism of scrub typhus is transmitted to human through the bite of chigger. These organisms are found throughout the mite's body, with the highest number resides in the salivary glands. When chigger feeds on mammals, including cattle, rodents or humans, the disease causing organisms are transmitted from the mite to a vertebrate host (subject). Scrub typhus infections are usually found in people engaged in activities that bring them inadvertently in contact with mite-infested habitats or any vertebrate host-carrier of these anthropods. These hosts may include domesticated or non-domesticated animals, such as cattle or rodents. These hosts may be carrying mites which have not begun to feed on them. In this case, the live mites can be transferred from the vertebrate host to people. Individuals particularly susceptible include butchers, meatworkers, animal-farm workers, and others engaged in outdoor activities. These persons could be infected by coming into contact with the mite-carrying animals. Additionally, rodents are capable of carrying and spreading infected mites to people in populated areas. Larval *Leptotrombidium* mites feed on vertebrate hosts. The larval mites acquire *O. tsutsugama* through their female parent. This type of pathogen reception is called "transovarial transmission."

Once transmitted to the host, the organism incubates for about 10 to 12 days before the onset of illness. Five to eight days after infection, a dull red rash and/or eschar may appear on the body, especially on the trunk. If left untreated, *O. tsutsugamushi* can cause up to 35% mortality. A recent report from India documented 17% case fatality rate (3). At the present time, no vaccine is available for protection against scrub typhus. Recent evidence of antibiotic resistance of *O. tsutsugamushi* further emphasizes the need for a scrub typhus vaccine (13, 14).

Diagnosis of scrub typhus is generally based on clinical presentation and patient history. However, differentiating scrub typhus from other acute tropical febrile illnesses such as leptospirosis, murine typhus, malaria, dengue fever, and viral hemorrhagic fevers can be difficult due to similarities in signs and symptoms. Highly sensitive polymerase chain reaction (PCR) methods have made it possible to detect *O. tsutsugamushi* at the onset of illness, when antibody titers are not high enough to be detected (41, 44, 48). PCR amplification of the 56 kDa protein gene has been demonstrated to be a reliable diagnostic method for scrub typhus (41, 46). Furthermore, different genotypes associated with different *Orientia* serotypes could be identified by analysis of variable regions of this gene without isolation of the organism (41, 42, 43, 46, 49). However, gene amplification often requires sophisticated instrumentation and expensive reagents, which are generally not available in the rural medical facilities. Current serodiagnostic assays, such as the indirect immunoperoxidase (IIP) test, the indirect immunofluorescent antibody (IFA) test or the microimmunofluorescent antibody (MIF) test, require propagation of rickettsiae in infected yolk sacs of embryonated chicken eggs or antibiotic free cell cultures (51).

Currently, the only commercially available dot-blot immunologic assay kit, DIP-S-Ticks Scrub Typhus Diagnostic Test Kit (Panbio, Queensland, Australia) requires steps of growing the disease causing organisms in tissue culture, purifying of the organisms using Renografin density gradient, and the extraction of the whole cell antigen (50). However, only a few specialized laboratories have the ability to culture and purify *O. tsutsugamushi* since these procedures must be carried out under biosafety level 3 (BL3) requirements. Furthermore, large-scale growth and purification of the *Orientia* are prohibitively expensive. Therefore, the availability of recombinant rickettsial protein antigens that can be produced and purified in large amounts and have similar sensitivity and specificity to *Orientia*-derived antigens, would greatly reduce the cost, transport, and reproducibility problems presently associated with diagnostic tests of scrub typhus.

*O. tsutsugamushi* also exhibits considerable strain variation (15-18). Homologous protection developed from natural infection persists for at least one year, but heterologous protection may remain for less than six months (19, 20). Both humoral and cell-mediated immune responses are important in protective immunity against scrub typhus (21-25). Prior vaccine development efforts using whole organism suggest that a scrub typhus vaccine is possible. Effective vaccination in mice has been achieved with a biovaccine comprising a single dose of live organisms in combination with chloramphenicol or a vaccine comprising gamma-irradiated live organisms (26, 27). Immunization of volunteers with live vaccine in combination with chloramphenicol prophylaxis elicited immunity comparable to that of natural infection (19). Although a recent report suggested that long-term adaptation in egg-yolk sac has increased the yield of *Orientia* (28), considerable difficulties still exist in mass production of purified *O. tsutsugamushi* and in retaining its stability upon storage. Consequently, whole cell vaccine products are unlikely to be economically feasible or suitable for manufacturing with current Good Manufacturing Practices Act standards of purity, potency, and lot-to-lot consistency. Furthermore, not every component in the whole cell antigen is protective. It has been demonstrated that the 22 kDa antigen not only did not provide any protection, but also inhibited the protection provided by other antigens (29). Therefore, it is essential to develop a subunit vaccine composed of genetically engineered antigens which are capable of inducing protective immunity in human subjects.

SUMMARY OF INVENTION

Accordingly, an object of this invention is recombinant chimeric antigens comprising modified and unmodified reactive polypeptide fragments of r56 protein from more than one strain of Orientia tsutsugamushi.

A still further object of the invention is a recombinant chimeric antigen which is re-folded to give a soluble moiety.

An additional object of this invention is the use of recombinant chimeric antigens in antibody based assays as improved methods for the detection of O. tsustugamushi exposure in research and in clinical samples.

Yet another object of this invention is the use of recombinant chimeric antigens for use in different vaccine formulations against scrub typhus infection.

These and other objects, features and advantages of the present invention are described in or are apparent from the following detailed description of preferred embodiments.

BRIEF DESCRIPTION OF DRAWINGS

FIG. 2A: Full length 56 kDa from Karp strain and Kp r56 Cloning sequence.

FIG. 2B: Full length 56 kDa from TA 763 and TA763r56 Cloning sequence.

FIG. 3A: Chimeric antigen 1 showing modifications to the variable domains of the 56 kDa protein antigens of Karp and TA763 strains.

FIG. 3B: Chimeric antigen 2 showing modifications to the variable domains of the 56 kDa protein antigens of Karp and TA763 strains.

FIG. 3C: Chimeric antigen 3 showing modifications to the variable domains of the 56 kDa protein antigens of Karp and TA763 strains.

DESCRIPTION OF EMBODIMENTS

Figure 1A:
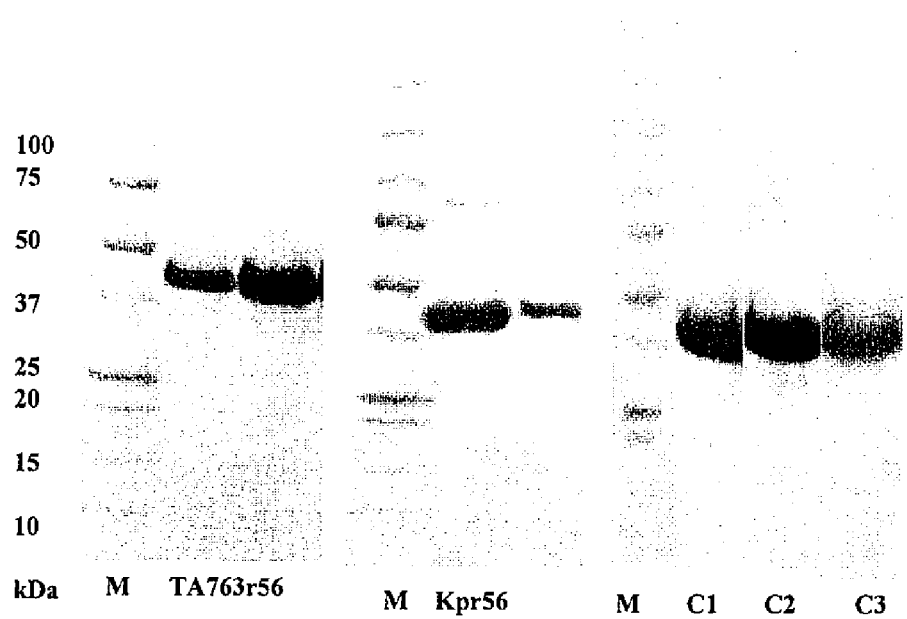
FIG. 1A: SDS-PAGE showing r56 protein antigens of TA763, Karp and chimeric antigen 1, 2 and 3 (C1, C2 and C3), all purified to achieve greater than 95% purity.

Western blot analysis of whole cell lysates with scrub typhus patient sera has identified at least four protein antigens of O. tsutsugamushi with molecular weights of 22 kDa, 47 kDa, 56 kDa and 110 kDa (30). Among them, the 56 kDa antigen is the naturally dominant protein antigen, which accounts for 10-15% of the total cell protein. Almost every clinically diagnosed patient serum reacts with 56 kDa antigen, but not every patient serum reacts with 22 kDa, 47 kDa or 110 kDa antigens (31, 32). In one study, only 15% (2/13) patient sera recognized the 47 kDa antigen (31). Recombinant 56 kDa protein (r56) has been shown to be protective in mice against homologous challenge (33-35). High titers of antibodies to O. tsutsugamushi were also detected in mouse sera. A dose-dependent pattern of lymphocyte proliferation and levels of IFN-gamma and IL-2 production (cytokine profile of Th1 cells) was observed in spleen mononuclear cells from immunized mice (33). The 56 kDa protein plays a role in the adhesion and internalization of O. tsutsugamushi into host cells (25). Both polyclonal and monoclonal antibodies against this antigen can block rickettsial infection of fibroblasts (36-38). All these results suggest that the 56 kDa protein is an ideal candidate for vaccine development.

A recombinant protein from Karp stain (Kp r56) has been developed, which has shown 60-100% protection from homologous challenge in an outbred mouse model. Moreover, it has been shown to be safe and immunogenic in the scrub typhus non-human primate model using Cynomolgus monkeys. This vaccine candidate has recently been evaluated for protection from heterologous challenge with 5 non-Karp strains of O. tsutsugamushi. Various degree of protection was observed in CD-1 mice challenged with Kato (56%), TA763 (45%), TH1812 (39%), TH1814 (33%), Citrano (11%). Co-administration of Karp (Kp) r56 and Kato (Kt) r56 resulted in similar protections against Karp, TA263 and TH1814 but increased somewhat for Kato, TH1812 and Citrano (Karp 67%, Kato 78%, TA763 33%, TH1812 67%, TH1814 33%, Citrano 45%). It has also been shown that mouse sera raised against TA 763 r56 (SEQ ID No. 4) reacted with many heterologous strains (39) and TA763 r56 reacts with sera of many serotypes, which suggests its broad reactivity. Recently, additional r56 antigens have been added to the Kp r56 to produce a multivalent vaccine (KpKtGm r56). This vaccine has shown some, but not complete heterologous protection.

Therefore, it is an objective of this invention to design a chimeric antigen using reactive polypeptide fragment from more than one strain of O. tsutsugamushi, including but not limited to Karp, Kato, Gilliam, TA763, TH1811, TH1812, TH1814, AFC27, 18032460, 18032404, Woods, Citrano, MAK119 and MAK243. Such recombinant chimeric antigen will offer broad cross reactivity among different stains and may be used in detection assays or as part of a vaccination composition against scrub typhus.

In an embodiment of the present invention, recombinant chimeric antigens 1, 2 and 3 are designed by making modifications to the variable domains of the 56 kDa protein antigens of the Karp and TA763 strains. This is an attempt to generate proteins that have potentially broad reactivity toward multiple strains of O. tsutsugamushi. The cross reactivity of these chimeric antigens were evaluated with strain-specific mouse sera and compared to the reactivity of r56s from Karp and TA763 strains. It is demonstrated that the chimeric protein antigens reacted very well with as many as 14 disparate strains of O. tsutsugamushi. The results suggested the possibility of combining minimum number of r56s to provide cross reactivity with the most strains of O. tsutsugamushi, and also indicating that the combination of these r56s in a vaccine formulation may provide a better protection for heterologous challenge.

Design of Chimeric Proteins

Figure 1B:
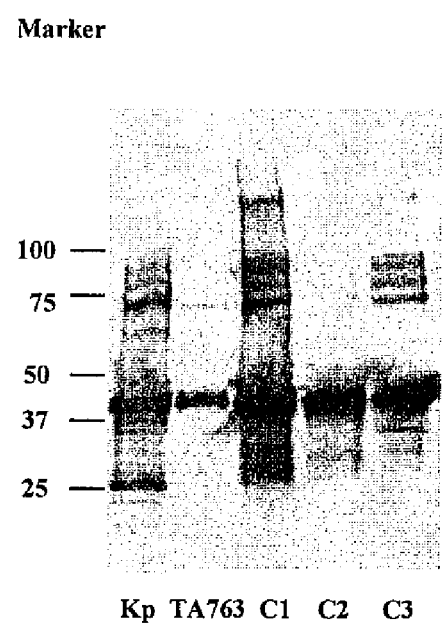
FIG. 1B: Western Blot result showing that all tested r56 proteins reacted with the specific antibody against the 56 kDa protein from Karp strain. The results suggest that there are cross reactivity between TA763r56, C1, C2 and C3 with antibody raised specifically against Kpr56.

The 56 kDa protein sequences from Karp and TA763 strains of O. tsutsugamushi were used as the building blocks for the chimeric proteins. Chimeric antigen 1 (C1) was designed to use the Karp 56 kDa protein sequence as the backbone while replacing its variable domain 1 (FIG. 2A) with the variable domain 1 of the 56 kDa protein antigen of the TA763 stain with a slight modification (FIG. 2B). The final sequence of C1 is set forth in SEQ ID No. 1 (FIG. 3A). Similar strategy was used in the design of chimeric antigen 2 (C2). Sequence of the 56 kDa protein of the TA763 strain (FIG. 2B) was used as the backbone for the chimeric antigen 2 with its variable domain 3 replaced with a slightly modified variable domain 3 of the 56 kDa protein antigen of the Karp strain (FIG. 2A). The sequence of C2 is set forth in SEQ ID No. 2 (FIG. 3B). Chimeric antigen 3 (C3) comprising the modified variable domains 1, 2 and 3 from Karp and TA763 strains. Variable domain 1 and 2 are based on the same domains of the 56 kDa protein antigen of the TA 763 stain but slightly modified (FIG. 2B), and variable domain 3 of C3 is based on variable domain 3 of the 56 kDa protein antigen of the Karp stain also with slight modification (FIG. 2A). The sequence of C3 is set forth in SEQ ID No. 3 (FIG. 3C). The DNA was synthesized by Bioclone (San Diego, Calif.) and cloned into pET29a vector (NOVAGEN®, Gibbstown, N.J.) with built-in NdeI and XhoI restriction sites. The resulting sequence was confirmed. Specific design strategy is shown in Table 1 (Appendix A)

Cloning of 56 kDa Protein Genes from Karp and TA763 Strains of *O. tsutsugamushi*

The primers with built-in BamH1 and NdeI restriction sites for the 56 kDa protein gene (amino acid 80-456 of the open reading frame) were designed based on the available DNA sequences of the Karp and TA763 strains in NCBI database. Respective strain of *O. tsutsugamushi* was purified from infected L929 cells using Renografin gradient (52). After gradient, the pure organisms were resuspended in water and freezed at −80° C. until use. DNA of each strain of *O. tsutsugamushi* was extracted using QiaAmp DNA mini kit (QIAGEN Inc., Valencia, Calif.) following the manufacturer's description. The purity of DNA was determined spectrophotometrically and the value of $OD_{260}/OD_{280}$ was greater than 1.8. The extracted DNA was then used as template in combination with appropriate primers for each specific strain in a polymerase chain reaction (PCR). The amplicons was cloned into a pET24a vector (NOVAGEN®, Gibbstown N.J.). Colonies were selected and the presence of amplicons was verified. Sequences of the amplicons were confirmed. The plasmid was transformed into BL21(DE3) cells for protein expression.

Expression of Recombinant 56 kDa Proteins from BL21 (DE3) Transformants

BL21(DE3) transformants containing correct amplicons were selected, grew in LB in the presence of 50 μg/mL kanamycin in a 37° C. shaker and agitated at 200 rpm. The cells were induced with 1 mM IPTG when $OD_{600}$ reached 0.8-1.0. After induction for 19 hours, the cells were centrifuged at 4000 rpm for 30 minutes in SS34 rotor to separate cells from LB medium. The wet weight of cell pellet was determined. At least 100 μL each of cell suspension prior to and post induction was removed to examine the level of induction. Samples with confirmed induction were processed for protein purification.

Extraction and Solubilization of Inclusion Bodies Containing the Recombinant 56 kDa Protein Three gram of cell pellet was resuspended in 15 ml of 2% Deoxycholate (DOC) in 20 mM Tris-HCl (pH 7.5) at a W/V ratio of 1:5 and dispersed well to ensure complete dissolution. Cell suspension was sonicated 6 times on ice at output setting of 3 for 10 seconds each. Cells were then spun at 10,000 rpm for 30 minutes at 4° C. The supernatant was removed and 2 M urea solution was added to the pellet. The pellets were dispersed well by up-down suction using a 10-ml pipette, and put it on a shaker for 30 min. The suspection was centrifuged and the surpernatant was discarded and 4 M urea in 20 mM Tris-HCl (pH 7.5) with the same volume as 2% DOC was to the pellet. The pellet was dispersed well and incubated for 30 min with gentle rocking. Centrifuged the solution at 10,000 rpm for 30 min at 4° C. and poured out the supernatant. Added 10 ml of 6 M urea in 20 mM Tris-Hcl, pH 7.5 to the pellet and dispersed the pellet well and incubated for 30 min with gentle rocking. The solution was centrifuged again under the same procedure and the supernatant was discarded. Added 10 ml of 8 M urea in 20 mM Tris-HCl, pH 7.5 to the pellet and dispersed the pellet well. The pellet was incubated for 30 min with gentle rocking on a shaker. The distribution of protein in each fraction was examined using SDS-PAGE. The supernatant (approx 10 ml) containing majority of chimeric proteins was in 6M-urea. This supernatant was collected in a 15-ml tube and stored in 4° C. before further purification.

Chromatographic Purification of r56 Proteins in the Presence of 6M Urea

The 6M urea supernatant containing recombinant protein (r56) was subjected to anion-exchange chromatography (DEAE, 21.5×15 cm) using Waters 2195 HPLC. The buffers used were 6 M urea in 20 mM Tris-HCl (final pH=8.0) containing 1 mM each of DTT and EDTA (solvent A), 500 mM NaCl in solvent A (elution buffer) and 2 M NaCl in solvent A (ending buffer). The DEAE column was equilibrated with starting buffer (solvent A) for at least column volume at 4 mL/min. The 6M urea supernatant was loaded onto the column through pump at 1 mL/min. Once the sample was loaded onto the column, the gradient started at 100% starting buffer for 25 minutes then in 10 minutes slowly increased to 6% elution buffer. The concentration of elution buffer was slowly ramped up to 14% in 50 minutes. Chimeric proteins were eluted within this period and collected at 0.15 minutes per fraction (0.6 mL). The DEAE column was further cleaned by using a 40 minutes run at 100% ending buffer to remove any residual amount of bound protein. The purity of protein in each fraction was accessed by running SDS-PAGE. The pure fractions were pooled together. If the purity of protein was not satisfactory (>95% purity as evidenced on an overloaded SDS-PAGE), a $2^{nd}$ run of DEAE chromatography was carried out after dialysis of the pooled fractions to remove NaCl. The procedure for the $2^{nd}$ DEAE was similar to the first DEAE purification but the gradient was modified so that elution buffer was slowly increased from 6% to 12% in 50 minutes. If necessary, 6M urea supernatant containing chimeric protein can be first purified by two gel filtration columns connected in tandem using solvent A as the buffer. The fractions containing chimeric protein can be pooled together and be purified by anion exchange chromatography as described. The final fractions containing chimeric protein were evaluated for protein purity using SDS-PAGE.

Refolding of Pure r56s by Dialysis

The dialysis tubing (SPECTRUM® Chemical and Laboratory Products, Gardena, Calif.) was boiled in sodium carbonate solution, rinsed with water and then stored in water containing 0.02% $NaN_3$ in 4° C. The volume of dialysis buffer and sample is 20:1 (i.e. 10 mL of sample in 200 mL dialysis buffer). The pure chimeric protein was in solvent A containing NaCl. Dialysis was done in a step-wise manner to remove NaCl and lower the concentration of urea from 6 M to none. First, the purified pooled fractions were transferred into the prepared dialysis tubing and dialyzed against 4M urea in solvent A for 30 minutes twice in cold room under gentle stirring. At the end of $2^{nd}$ dialysis against 4M urea, replaced the 4M urea with 2M urea and dialyzed the sample the same way. Then replaced 2M urea with 1M urea and dialyzed for the same period using the same dialysis procedure. Finally, replaced 1M urea with 20 mM Tris-HCl (pH7.5) and dialyzed for the same period.

Protein Purification and Western Blot Verification

All the r56s were purified to greater than 95% purity (FIG. 1A). In all cases, protein was over loaded in each lane to ensure purity. Same amount of each r56 was loaded onto the gel for western blot. FIG. 1B shows that all r56s reacted with the specific antibody against the 56 kDa protein from Karp strain. This result suggests that there are cross reactive epitopes in TA763r56, C1, C2 and C3, which can be recognized by antibody raised specifically against Kpr56. The dialyzed chimeric r56s was analyzed by SDS-PAGE to examine the purity. Gel was transferred onto PVDF membrane using standard procedure. The PVDF membrane was stained with CodeBlue staining solution to visualize protein bands. The single band between 37 and 50 kDa was cut out of the membrane and analyzed by protein N-terminal sequencer (Applied Biosystems 490, Applied Biosystems, Foster City, Calif.) to confirm the expressed protein was the designed 56 kDa protein. Additional gel was transferred onto nitrocellulose membrane. The nitrocellulose membrane was blotted by 10% milk in TBS-tween20 (TBST) for 1 h with gentle agitation. Membrane was then washed with TBST for 5 minutes 3 times with agitation. Primary antibody against the 56 kDa protein antigen was added to 5% milk in TBST and incubated with membrane for 1 h at room temperature with gentle agitation. The membrane was then washed three times at 5 minutes each. HRP conjugated anti-mouse IgG antibody was the $2^{nd}$ antibody and was incubated with membrane in 5% milk in TBST for 1 hour. The membrane was then washed and incubated with peroxidase substrate (Bio-Rad Laboratories, Hercules, Calif.) for up to 30 minutes for development. The presence of a band between 37 and 50 kDa indicated the positive reactivity between the chimeric protein and antibody against 56 kDa protein (FIG. 1B).

Example 2

Analysis of Reactivity of Various r56s Protein and Sera from Mice Infected by Various Strains of *O. tsutsugamushi*

The cross reactivity of the three chimeric r56s were analyzed using strain-specific mouse sera. These strains (Table 2) are reported in regions within the scrub typhus endemic area.

TABLE 2

Geographic Distribution of different *O. tsutsugamushi* strains tested

| Location | Strain name |
|---|---|
| Malaysia | 18032460, 18032404 |
| Thailand | TH-1811, TH1812, TH1814, AFC-27, TA763 |
| Japan | Kato |
| Burma | Gilliam |
| New Giunea | Karp |
| Taiwan | MAK119, MAK243 |
| Australia | Woods, Citrano |

In order to know whether the design of chimeric protein has improved cross reactivity, the parent r56s (Kpr56 and TA763r56) were also analyzed using the same set of sera.

The concentration of each protein antigen (Kpr56, TA763r56, C1, C2 and C3) was determined by Bradford method. A preliminary study had established that the amounts of antigen required to coat the plate was 0.3 μg/well (total volume was 100 μL). Therefore, the concentration of each chimeric protein antigen was adjusted to 0.3 μg/100 μL by 0.2×PBS. The plate was coated at 4° C. overnight. On the day of experiment, plates were first washed 3 times with 1×PBS containing 0.1% TWEEN® 20 (1×PBST). The plates were then blocked with 200 μL/well of 10% milk in 1×PBST and were incubated for 1 hour at room temperature. Primary antibody (mouse sera) was diluted in 5% milk in 1×PBST. The primary antibody was diluted 1:100 for screening purpose. For titration purpose, primary antibody was prepared for a serial dilution differed by a factor of 4 (1:100, 1:400, 1:1600 etc). After blocking, plates were washed 3 times with 1×PBST and 100 μL/well of diluted primary antibody were added. Plates were incubated for 1 hour at room temperature. After incubation, Plates were washed 3 times with 1×PBST. HRP conjugated goat anti-mouse IgG was used as the secondary antibody. The antibody was diluted to 1:4000 in 5% milk in 1×PBST and 100 μL/well of diluted secondary antibody was applied and plates were incubated for 1 hour at room temperature. At the end of incubation, plates were washed 3 times with 1×PBST. A 1:1 ratio of ABTS® Peroxidase Substrate Solution A and Peroxidase Substrate Solution B (Kirkegaard & Perry Laboratories, Gaithersburg, Md.) was prepared and added at 100 μL/well. Plates were incubated for 15-30 minutes in a dark drawer. Plates were read after 30 minutes incubation at 405 nm-650 nm on an UVmax kinetic microplate reader (Molecular Devices, Philadelphia, Pa.).

Evaluation of Cross Reactivity of r56 with Mouse Sera by ELISA.

Among these strains, immunization by r56 was not protective to subsequent challenged by MAK119 and 243 in the mouse model. Therefore, serum collected from the patients who were infected with these two strains was used for the evaluation. All the tested sera when diluted 100 folds reacted with every r56. The titer of each serum was determined for the 5 r56s as a measurement of reactivity. There is reactivity differences among the r56s. Kpr56 and TA763r56 had the highest titers with sera from respective homologous infection challenge (Table 3), confirming the expected hypothesis that these antigens are most reactive toward its own antibodies. In addition to the reactivity with homologous serum, Kpr56 was the most reactive antigen for sera from Th1812, 18032460, 18032404, Woods, Citrano infected mice. TA763r56 was the most reactive antigen for TH1811, TH1812, TH1814, AFC-27, 18032404, Woods, Citrano and MAK243 (Table 3). Chimeric antigens C1, C2 and C3, behaved similarly for any of the given serum (Table 4).

TABLE 3

Measurement of reactivity of Kpr56 and TA763r56 with 14 mouse sera using ELISA[a]

| | Antigen used | |
|---|---|---|
| Sera strain | Kpr56 | TA763r56 |
| Karp | 25,600[b] | 1,600 |
| Kato | 1,600 | 1,600 |
| Gilliam | 6,400 | 25,600 |
| TA763 | 25,600 | 102,400 |
| TH1811 | 6,400 | 25.600 |
| TH1812 | 6,400 | 25,600 |
| TH1814 | 25,600 | 25,600 |
| AFC27 | 6,400 | 25,600 |
| 18032460 | 25,600 | 6,400 |
| 18032404 | 25,600 | 25,600 |
| Woods | 25,600 | 25,600 |
| Citrano | 6,400 | 6,400 |
| MAK119 | 1,600 | 1,600 |
| MAK243 | 6,400 | 25,600 |

[a]ELISA was performed as described in Materials and Methods. All the sera were from mice with the exception of MAK119 and MAK243 which were from human. The positive cutoff was at least the average $OD_{405}$ for negative sera + 2 S.D. In the case of mouse sera, the cutoff was 0.1. For MAK119 and MAK243, the cutoff was 0.6.
[b]The titers highlighted in red are those sera showed highest titers with Kpr56 and the titers highlighted in blue are those sera showed highest titers with TA763r56.

TABLE 4

Measurement of reactivity of chimeric r56s with 14 strain specific mouse sera and 2 patient sera in ELISA[a]

| Sera strain[b] | Antigen used | | |
|---|---|---|---|
| | C1 | C2 | C3 |
| Karp | 6,400[c] | 1,600 | 1,600 |
| Kato | 1,600 | 1,600 | 1,600 |
| Gilliam | 25,600 | 6,400 | 25,600 |
| TA763 | 25,600 | 25,600 | 25,600 |
| TH1811 | 6,400 | 6,400 | 6,400 |
| TH1812 | 6,400 | 6,400 | 6,400 |
| TH1814 | 25,600 | 25,600 | 6,400 |
| AFC27 | 6,400 | 6,400 | 6,400 |
| 18032460 | 25,600 | 6,400 | 6,400 |
| 18032404 | 25,600 | 6,400 | 25,600 |
| Woods | 25,600 | 6,400 | 25,600 |
| Citrano | 6,400 | 6,400 | 6,400 |
| MAK119 | 1,600 | 6,400 | 1,600 |
| MAK243 | 25,600 | 25,600 | 25,600 |

[a]ELISA was performed as described in Materials and Methods. All the sera were from mice with the exception of MAK119 and MAK243 which were from human. The positive cutoff was at least the average of $OD_{405}$ for negative sera + 2 S.D. In the case of mouse sera, the cutoff was 0.1. For MAK119 and MAK243, the cutoff was 0.6.
[b]The bold strains are those with the same titers in at least one of chimerics and the parent Kpr56 and/or TA763r56.
[c]The titers highlighted in red are those sera showed highest titers among the chimerics with C1, in blue are those sera with C2 and in green are those with C3.

Furthermore, for most tested sera with the exception of Karp, TA763, TH1811 and TH1812, the chimeric antigens (C1, C2 and C3) were as reactive as either Kpr56 or TA763r56. These results suggested that although the sequence modifications were made on the parent 56 kDa protein, these chimeric antigens still retained similar reactivity with most sera. Therefore raise the potential to use one of the three chimeric antigens as substitution of both Kpr56 and TA763r56. When comparison was made only among the chimeric antigens, C1 appeared to be the best antigen as it had the highest titers against all 14 sera. In fact, the titers with C1 were as high as those for Kpr56 or TA763r56 for the seven tested sera. Although it is hard to correlate the titer against a specific antigen with the overall stimulation of immune responses, measurement of titers does provide information about the reactivity of certain antigen to antibodies. It is thus plausible that these chimerics can be used as reagents for diagnostic purpose as well as vaccine candidates.

Example 3

Evaluation of Protective Efficacy of Chimeric Antigens in Mouse Challenge Model CD1 female mice were immunized with r56s and subsequently challenged to evaluate the protective efficacy provided by individual r56. Ten mice were immunized with 25 μg of each protein antigen subcutaneously with CpG (aligo 1826) and montanide as adjuvants according to experiment design. Challenge was performed by intraperitoneal injection of live *O. tsutsugamushi* and the mice were monitored for additional 21 days. Previous experiments have demonstrated that one or two immunizations using Kpr56 offers poor heterologous protection. Therefore, the mice were given three immunizations in this study at four-week interval.

Homologous challenges were performed to compare the protective effect of these chimeric proteins to their parental proteins (i.e. Kpr56 and TA763r56). We found that chimeric antigen 1 and 2 provided similar or better protection than Kpr56 against Karp strain challenge. Although none of the chimeric provided better protection than TA763r56 against TA763 challenge, partial protection was observed by all chimerics. The results demonstrated that these chimeric protein antigens can provide excellent homologous protection against Karp strain and partial protection against heterologous TA763 strain. Further studies are needed to compare the protective efficacy of TA763r56 or Kpr56 against heterlogous challenges with that of chimeric proteins. The combination of chimeric proteins may provide a broader protection.

TABLE 5

Evaluation of protective efficacy of recombinant protein antigens in mouse challenge model.

| Group | Immunogen[a] | Challenge strain and dosage | Protective efficacy |
|---|---|---|---|
| 1 | PBS | 1000 × LD50 (Karp)[b] | 0 |
| | | 500 × LD50 (Karp)[c] | 0 |
| | | 60 × LD50 (TA763)[b] | 0 |
| | | 5 × LD50 (TA763)[c] | 0 |
| 2 | Kpr56 | 1000 × LD50 (Karp) | 63 |
| | | 500 × LD50 (Karp) | 50 |
| 3 | Chimeric 1 | 1000 × LD50 (Karp) | 75 |
| | | 500 × LD50 (Karp) | 56 |
| | | 60 × LD50 (TA763) | 40 |
| | | 5 × LD50 (TA763) | 13 |
| 4 | Chimeric 2 | 1000 × LD50 (Karp) | 75 |
| | | 500 × LD50 (Karp) | 90 |
| | | 60 × LD50 (TA763) | 20 |
| | | 5 × LD50 (TA763) | 13 |
| 5 | Chimeric 3 | 1000 × LD50 (Karp) | 38 |
| | | 60 × LD50 (TA763) | 30 |
| 6 | TA763r56 | 60 × LD50 (TA763)[b] | 90 |
| | | 5 × LD50 (TA763)[c] | 50 |

[a]Immunogens used are r56 protein antigen from Karp (Kpr56) and TA763 (TA763r56) strains and 3 chimeric r56 protein antigens as described previously.
[b]Mice were immunized three times at 4-week interval. Challenge were done 4 weeks after the last immunization.
[c]Mice were immunized three times at 2-week interval. Challenge were done 2 weeks after the last immunization.

Because these newly made chimeric proteins were similarly reactive with sera as the parent proteins, one can use one of the three chimerics, particularly C1 to substitute the parent proteins for use in diagnosis of *O. tsutsugamushi* infection or as vaccine candidates to improve the broad protective efficacy.

An embodiment of the invention is an assay for detecting antibody to scrub typhus comprising:
    a. obtaining a sample from a subject;
    b. exposing the sample to a recombinant chimeric antigen in assay equipment selected from the group consisting of Elisa plates, dot-blot matrices, and hand held chromatographic and flow through assay devices;
    wherein said chimeric antigen containing unmodified and modified reactive polypeptide fragments from more than one strains of *Orientia tsutsugamushi*, such as the chimeric antigen proteins C1, C2 and C3 as described in previous sections.

It is possible that similar approach can be made to generate more chimerics based on 56 kDa protein sequences from different strains in order to minimize the number of proteins included in the final vaccine formula yet still provide a very broad protection against most number of strains possible.

CITATION LIST

1. Brown G W, Robinson D M, Huxsoll D L, Ng T S, Lim K J, Sannasey G. Scrub typhus: a common cause of illness in indigenous populations. Trans R Soc. Trop Med Hyg. 1976; 70:444-8.
2. Kawamura A, Tanaka H, Tamura A. 1995. Tsutsugamushi Disease. Tokyo: University of Tokyo Press.
3. Kumar K, Saxena V K, Thomas T G, Lal S. Outbreak investigation of scrub typhus in Himachal Pradesh (India). J Commun Dis. 2004 December; 36(4):277-83.

4. Chang W-H. Current status of tsutsugamushi disease in Korea. J. Korean Med. Sci. 1995; 10:227-38.
5. Jiang J, Marienau K J, May L A, Beecham H J, Wilkinson R, Ching W-M, Richards A L. Laboratory diagnosis of two scrub typhus outbreaks at Camp Fuji, Japan in 2000 and 2001 by enzyme-linked immunosorbent assay, rapid flow assay, and Western blot assay using outer membrane 56-kD recombinant proteins. Am J Trop Med Hyg. 2003; 69(1): 60-6.
6. Sharma A, Mahajan S, Gupta M L, Kanga A, Sharma V. Investigation of an outbreak of scrub typhus in the himalayan region of India. Jpn J Infect Dis. 2005 August; 58(4): 208-10.
7. Wang S, Huang J, Peng G, Jiang P, Zheng N, Liu J, Zhu S, Wang Z. Natural foci of tsutsugamushi disease in the Nan Peng Lie Islands in China. Chin Med J (Engl). 2002; 115 (2):272-5.
8. Lewis M D, Yousuf A A, Lerdthusnee K, Razee A, Chandranoi K, Jones J W. Scrub typhus reemergence in the Maldives. Emerg Infect Dis. 2003; 9(12):1638-41.
9. Durand A M, Kuartei S, Togamae I, Sengebau M, Demma L, Nicholson W, O'Leary M. Scrub typhus in the Republic of Palau, Micronesia. Emerg Infect Dis. 2004 October; 10 (10):1838-40.
10. Tay S T, Kamalanathan M, Rohani M Y. Antibody prevalence of *Orientia tsutsugamushi, Rickettsia typhi* and TT118 spotted fever group rickettsiae among Malaysian blood donors and febrile patients in the urban areas. Southeast Asian J Trop Med Public Health. 2003 March; 34; (1):165-70.
11. Odorico D M, Graves S R, Currie B, Catmull J, Nack Z, Ellis S, Wang L, Miller D J. New *Orientia tsutsugamushi* strain from scrub typhus in Australia. Emerg Infect Dis. 1998 October-December; 4(4):641-4.
12. Lee Y S, Wang P H, Tseng S J, Ko C F, Teng H J. Epidemiology of scrub typhus in eastern Taiwan, 2000-2004. Jpn J Infect Dis. 2006 August; 59(4):235-8.
13. Watt G, Chouriyagune C, Ruangweerayud R, Watcharapichat P, Phulsuksombati D, Jongsakul K, Teja-Isavadham P, Bhodhidatta K, Corcoran K D, Dasch G A, Strickman D. Scrub typhus poorly responsive to antibiotics in northern Thailand. Lancet. 1996; 348:86-9.
14. Mathai E, Rolain J M, Verghese G M, Abraham O C, Mathai D, Mathai M, Raoult D. Out break of scrub typhus in southern India during the cooler months. Ann New York Acad Sci. 2003; 990:359-64.
15. Bell E J, Bennett L F, Whiteman L. Antigenic differences between strains of scrub typhus as demonstrated by cross neutralization tests. Proc Soc Exp Bio Med. 1946; 62:134-7.
16. Rights F L, Smadel J E, Jackson E B. Studies on scrub typhus (tsutsugamushi disease). Part III: Heterogeneity of strains of *Rickettsia tsutsugamushi* as demonstrated by cross vaccination studies. J Exp Med. 1948; 87:339-351.
17. Bennett L F, Patt J K, Hopps H E. Studies on scrub typhus (tsutsugamushi disease). Part IV: Heterogeneity of strains of *R. tsutsugamushi* as demonstrated by cross-neutralization tests. J Immunol. 1949; 62:453-61.
18. Kang J S, Chang W H. Antigenic relationship among the eight prototype and new serotype strains of *Orientia tsutsugamushi* revealed by monoclonal antibodies. Microbiol Immunol. 1999; 43:229-234.
19. Smadel J E, Ley H L, Diercks F H, Paterson P Y, Wisseman C L, Traub R. Immunization against scrub typhus: duration of immunity in volunteers following combined living vaccine and chemoprophylaxis. Am J Trop Med Hyg. 1952; 1:87-99.
20. Smadel J E, Ley H L, Diercks F H, Traub R. Immunity in scrub typhus: resistance to induced reinfection. Arch Pathol. 1950; 50:847-861.
21. Jerrells T R, Osterman J V. Host defenses in experimental scrub typhus: deplayed-type hypersensitivity responses of inbred mice. Infect Immun. 1982; 35:117-123.
22. Jerrells T R, Osterman J V. Development of specific and crossreactive lymphocyte proliferative responses during chronic immunizing infections with *Rickettsia tsutsugamushi*. Infect Immun. 1983; 40(1):147-56.
23. Hickman C J, Stover C K, Joseph S W, Oaks E V. Murine T-cell response to native and recombinant protein antigens of *Rickettsia tsutsugamushi*. Infect Immun. 1993; 61(5): 1674-81.
24. Seong S Y, Kim M K, Lee S M, Odgerel Z, Choi M S, Han T H, et al. Neutralization epitopes on the antigenic domain II of the *Orientia tsutsugamushi* 56-kDa protein revealed by monoclonal antibodies. Vaccine. 2000; 19(1):2-9.
25. Hanson B A. Effect of immune serum on infectivity of *Rickettsia tsutsugamushi*. Infect Immun. 1983; 42:341-9.
26. Kekcheyeva N. Preventive immunization against tsutsugamushi fever. J Hyg Epidemiol Microbiol Immunol. 1968; 12:14-7.
27. Eisenberg G H G, Osterman. J V. Experimental scrub typhus immunogens: gamma-irradiated and formalinized rickettsiae. Infect Immun. 1977; 15:124-31.
28. Choi Y, Kim K S, Kim T Y, Cheong H S, Ahn B Y. Long-term egg-yolk adaptation of the *Orientia tsutsugamushi* for preparation of a formalinized immunogen. Vaccine. 2006; February; 24(9):1438-45.
29. Chao C C, Chan T C, Chattopadhyay S, Richards A L, Ching W M. DNA vaccine plasmid expressing the 22 kDa protein of *Orientia tsutsugamushi* inhibited the protections provided by DNA vaccine plasmids expressing other antigen genes in a mouse lethal challenge model. ASM General Meeting, New Orleans, La. May 23-27, 2004.
30. Tamura, A., H. Sakurami, K. Takahashi, and M. Oyanagi. 1985 Analysis of polypeptide composition and antigenic components of *Rickettsia tsutsugamushi* by polyacrylamide gel electrophoresis and immunoblotting. Infect. Immum. 48:671-675.
31. Ohashi N, Tamura A, Suto T. Immunoblotting analysis of anti-rickettsial antibodies produced in patients of tsutsugamushi disease. Microbiol Immunol. 1988; 32(11):1085-92.
32. Tay S T, Rohani M Y, Ho T M, Devi S. Antigenic types of *Orientia tsutsugamushi* in Malaysia. Southeast Asian J Trop Med Public Health. 2002 September; 33(3):557-64.
33. Seong S Y, Huh M S, Jang W J, Park S G, Kim J G, Woo S G, Choi M S, Kim I S, Chang W H, Induction of homologous immune response to *Rickettsia tsutsugamushi* Boryong with partial 56-kilodalton recombinant antigen fused with the maltose-binding protein MBP-Bor56. Infect Immun. 1997; 65:1541-45.
34. Yu Y, Wen B, Wen B, Niu D, Chen M, Qiu L. Induction of protective immunity against scrub typhus with a 56-kilodalton recombinant antigen fused with a 47-kilodalton antigen of *Orientia tsutsugamushi* Karp. Am J Trop Med Hyg. 2005; 72:458-64.
35. Ching W M, Richards A L, Chan T C, Chao C C, Chattopadhay S, Yang Q, Jiang J, Dasch G A, Oaks E, Kuminski R, Wang R, Shih J, Protection against scrub typhus by a truncated 56 kDa outer membrane protein antigen in the presence of various adjuvants. Manuscript will be ready for submission in December 2006.
36. Seong S Y, Kim H R, Huh M S, Park S G, Kang J S, Han T H, Choi M S, Chang W H, Kim I S. Induction of neu- 36. tralizing antibody in mice by immunization with recombinant 56 kDa protein of *Orientia tsutsugamushi*. Vaccine 1997; 15(16):741-7.
37. Seong S Y, Kim M K, Lee S M, Odgerel Z, Choi M S, Han T H, Kim I S, Kang J S, Lim B U. Neutralization epitopes on the antigenic domain II of the *Orientia tsutsugamushi* 56-kDa protein revealed by monoclonal antibodies. Vaccine. 2000; 19:2-9.
38. Moree M F. 1992. Structural, antigenic, and biological characterization of *Rickettsia tsutsugamushi* antigenic proteins. Ph. D. Dissertation. Dept. of Microbiology and Immunology, School of Medicine, U. Maryland at Baltimore.
39. Shirai A, Robinson D M, Brown G W, Gan E, Huxsoll D L. Antigenic analysis by direct immunofluorescence of 114 isolates of *Rickettsia tsutsugamushi* recovered from febrile patients in rural Malaysia. Jpn J Med Sci Biol. 1979 December; 32(6):337-44.
40. Brown, G. W., J. P. Saunders, S. Singh, D. L. Huxsoll, and A. Shirai. 1978. Single dose doxycycline therapy for scrub typhus. Trans. R. Soc. Trop. Med. Hyg. 72:412-416.
41. Furuya, Y., Y. Yoshida, T. Katayama, F. Kawamori, S. Yamamoto, N. Ohashi, A. Kamura, and A. Kawamura, Jr. 1991. Specific amplification of *Rickettsia tsutsugamushi* DNA from clinical specimen by polymerase chain reaction. J. Clin Microbiol. 29: 2628-2630.
42. Horinouchi, H., K. Murai, A. Okayama, Y. Nagatomo, N. Tachibana, and H. Tsubouchi. 1996. Genotypic identification of *Rickettsia tsutsugamushi* by restriction fragment length polymorphism analysis of DNA amplified by the polymerase chain reaction. Am. J. Trop. Med. Hyg. 54:647-651.
43. Kelly, D. J., G. A. Dasch, T. C. Chye, and T. M. Ho. 1994. Detection and characterization of *Rickettsia tsutsugamushi* (Rickettsiales: Rickettsiaceae) in infected *Leptotrombidium* (*Leptotrombidium*) fletcheri chiggers (Acari: Trombiculidae) with the polymerase chain reaction. J. Med. Entomol. 31:691-699.
44. Kelly, D. J., D: Marana, C. Stover, E. Oaks, and M. Carl. Detection of *Rickettsia tsutsugamushi* by gene amplification using polymerase chain reaction techniques. Ann. N.Y. Acad. Sci. 590:564-571.
45. Kelly, D. J., P. W. Wong, E. Gan, and G. E. Lewis, Jr. 1988. Comparative evaluation of the indirect immunoperoxidase test for the serodiagnosis of rickettsial disease. Am. J. Trop. Med. Hyg. 38:400-406.
46. Ohashi, N., Y. Koyama, H. Urakami, M. Fukuhara, A. Tamura, F. Kawamori, S. Yamamoto, S. Kasuya, and K. Yoshimura. 1996. Demonstration of antigenic and genotypic variation in *Orientia tsutsugamushi* which were isolated in Japan, and their classification into type and subtype. Microbiol. Immunol. 40:627-638.
47. Robinson, D. M., G. Brown, E. Gan, and D. L. Huxsoll. 1976. Adaptation of a microimmunofluorescence test to the study of human *Rickettsia tsutsugamushi* antibody. Am. J. Trop. Med. Hyg. 25:900-905.
48. Sugita, Y., T. Nagatani, K Okuda, Y. Yoshida, and H. Nakajima. 1992. Diagnosis of typhus infection with *Rickettsia tsutsugamushi* by polymerase chain reaction. J. Med. Microbiol. 37:357-360.
49. Tamura, A., N. Ohashi, Y. Koyama, M. Fukuhara, F. Kawamori, M. Otsuru, P-F. Wu, and S-Y. Lin. 1997. Characterization of *Orientia tsutsugamushi* isolated in Taiwan by immunofluorescence and restriction fragment length polymorphism analyses. FEMS Microbiol. Lett. 150:225-231.
50. Weddle, J. R., T. C. Chan, K. Thompson, H. Paxton, D. J. Kelly, G. Dasch, and D. Strickman. 1995. Effectiveness of a dot-blot immunoassay of anti-*Rickettsia tsutsugamushi* antibodies for serologic analysis of scrub typhus. Am. J. Trop. Med. Hyg. 53:43-46.
51. Bozeman, F. M., and B. L. Elisberg. 1963. Serological diagnosis of scrub typhus by indirect immunofluorescence. Proc. Soc. Exp. Biol. Med. 112:568-573.
52. Suwanabun N, Chouriyagune C, Eamsila C, Watcharapichat P, Dasch G A, Howard R S, Kelly D J. Evaluation of an enzyme-linked immunosorbent assay in Thai scrub typhus patients. Am J Trop Med Hyg. 56(1):38-43. (1997)

TABLE 1

APPENDIX A:

```
Considerations:  VDI: strain specific
                 VDII: cross reactive
                 VDIII: no antibody response (conformational epitopes?)
                 VDIV: strain specific (Karp and TA763 are very similar)

Chimeric 1 (based on Karp)
VDI(TA763 with modif.) + VDII(Kp) + VDIII(Kp) + Const(Kp) + VDIV(Kp)

Karp    GFRAEIGVMYLTNITAQVEEGKVKADSVGETKADSVGGK
Chim1   SFRAELGVMYLRNITAQVEEGKVKADSGSKTKADSGGET  (seq-1)
TA763   SIRAELGVMYLRNISAEVELGKVKADSGSKTKADSGGET Chimeric 2 (based on TA763) Change Y106 to C106
VDI(TA763) + VDII(TA763) + VDIII(Kp with modif.) + Const(Kp or TA) +
VDIV(Kp)

Karp    GPMVINPILLNIPQGNPNPVGNPPQRANPPAGFAIHNHEQWRH-L

Chim2   GPMMINPILLNIPQGNPNAQGNPPQRANPPAGFNIHNHEQWRH-F  (seq-2)

TA763   GRMMVNPVLLNIPQGPP--AQNP--RAAMQP-CNILDHDHWKH-

Chimeric 3 All three variable domains are modified, plus Change Y106
to C106
VDI(TA763 with modif.Seq-1) + VDII(TA763 with modif.Seq-3) + VDIII(Kp
with modif.Seq-2) + Const(Kp or TA) VDIV(Kp)
```

What is claimed is:

1. A recombinant chimeric protein comprising modified and unmodified reactive polypeptide fragments from more than one strains of *Orientia tsutsugamushi*, wherein said chimeric protein comprising the amino acid sequence set forth in SEQ ID NO.: 1.

2. The recombinant chimeric antigen of claim 1, wherein said *Orientia tsutsugamushi* stains are selected from the group consisting of: Karp, Kato, Gilliam, TA763, TH1811, TH1812, TH1814, AFC27, 18032460, 18032404, Woods, Citrano, MAK119, MAK243 and a combination thereof.

3. The recombinant chimeric antigen of claim 1, wherein said reactive polypeptide fragment is a refolded fragment of expression product of truncated non-fusion r56 kDa gene of *Orientia tsutsugamushi*.

4. An assay for detecting antibody to scrub typhus comprising:
   a. obtaining a sample from a subject and
   b. exposing the sample to recombinant chimeric antigen in assay equipment selected from the group consisting of Elisa plates, dot-blot matrices, and hand held chromatographic and flow through assay devices; wherein said chimeric antigen containing unmodified and modified reactive polypeptide fragments from more than one strains of *Orientia tsutsugamushi*, wherein said chimeric protein is the amino acid sequence set forth in SEQ ID NO.: 1.

5. An assay according to claim 4, wherein said recombinant chimeric antigen is for the detection of prior exposure to scrub typhus in subjects.

6. An assay according to claim 4, wherein said reactive polypeptide fragment is a refolded fragment of expressed product of the truncated non-fusion 56 kDa gene of *Orientia tsutsugamushi*.

7. A method for inducing an immune response to *Orientia tsutsugamushi*, comprising administering the chimeric antigen of claim 1, with a suitable pharmaceutically-acceptable carrier to a subject.

* * * * *

SEQUENCE LISTING

<160> NUMBER OF SEQ ID NOS: 5

<210> SEQ ID NO 1
<211> LENGTH: 377
<212> TYPE: PRT
<213> ORGANISM: Orientia tsutsugamushi
<220> FEATURE:
<221> NAME/KEY: MISC_FEATURE
<223> OTHER INFORMATION: Chimeric protein 1 based on sequences of
      recombinant r56 protein of multiple stains

<400> SEQUENCE: 1

Met Thr Ile Thr Pro Ser Phe Arg Ala Glu Leu Gly Val Met Tyr Leu
1               5                   10                  15

Arg Asn Ile Thr Ala Gln Val Glu Glu Gly Lys Val Lys Ala Asp Ser
                20                  25                  30

Gly Ser Lys Thr Lys Ala Asp Ser Gly Gly Glu Thr Asp Ala Pro Ile
            35                  40                  45

Arg Lys Arg Phe Lys Leu Thr Pro Pro Gln Pro Thr Ile Met Pro Ile
        50                  55                  60

Ser Ile Ala Asp Arg Asp Phe Gly Ile Asp Pro Asn Ile Pro Gln
65                  70                  75                  80

Gln Gln Ala Gln Ala Ala Gln Pro Gln Leu Asn Asp Glu Gln Arg Ala
                85                  90                  95

Ala Ala Arg Ile Ala Trp Leu Lys Asn Cys Ala Gly Ile Asp Tyr Arg
            100                 105                 110

Val Lys Asn Pro Asn Asp Pro Asn Gly Pro Met Val Ile Asn Pro Ile
        115                 120                 125

Leu Leu Asn Ile Pro Gln Gly Asn Pro Asn Pro Val Gly Asn Pro Pro
    130                 135                 140

Gln Arg Ala Asn Pro Pro Ala Gly Phe Ala Ile His Asn His Glu Gln
145                 150                 155                 160

Trp Arg His Leu Val Val Gly Leu Ala Ala Leu Ser Asn Ala Asn Lys
                165                 170                 175

Pro Ser Ala Ser Pro Val Lys Val Leu Ser Asp Lys Ile Thr Gln Ile
            180                 185                 190

Tyr Ser Asp Ile Lys Pro Phe Ala Asp Ile Ala Gly Ile Asp Val Pro
        195                 200                 205

Asp Thr Ser Leu Pro Asn Ser Ala Ser Val Glu Gln Ile Gln Asn Lys
    210                 215                 220

Met Gln Glu Leu Asn Asp Leu Leu Glu Glu Leu Arg Glu Ser Phe Asp
225                 230                 235                 240

Gly Tyr Leu Gly Gly Asn Ala Phe Ala Asn Gln Ile Gln Leu Asn Phe
                245                 250                 255

Val Met Pro Gln Gln Ala Gln Gln Gly Gln Gly Gln Gln Gln Gln
            260                 265                 270

Ala Gln Ala Thr Ala Gln Glu Ala Val Ala Ala Ala Val Arg Leu
        275                 280                 285

Leu Asn Gly Asn Asp Gln Ile Ala Gln Leu Tyr Lys Asp Leu Val Lys
    290                 295                 300

Leu Gln Arg His Ala Gly Ile Lys Lys Ala Met Glu Lys Leu Ala Ala
305                 310                 315                 320

Gln Gln Glu Glu Asp Ala Lys Asn Gln Gly Glu Gly Asp Cys Lys Gln
                325                 330                 335

Gln Gln Gly Thr Ser Glu Lys Ser Lys Lys Gly Lys Asp Lys Glu Ala

```
                    340                 345                 350
Glu Phe Asp Leu Ser Met Ile Val Gly Gln Val Lys Leu Tyr Ala Asp
        355                 360                 365

Val Met Ile Thr Glu Ser Val Ser Ile
        370                 375

<210> SEQ ID NO 2
<211> LENGTH: 377
<212> TYPE: PRT
<213> ORGANISM: Orientia tsutsugamushi
<220> FEATURE:
<221> NAME/KEY: MISC_FEATURE
<223> OTHER INFORMATION: Chimeric protein 2 based on sequence of
      recombinant r56 proteins from multiple strains

<400> SEQUENCE: 2

Met Thr Ile Thr Pro Ser Ile Arg Ala Glu Leu Gly Val Met Tyr Leu
1               5                   10                  15

Arg Asn Ile Ser Ala Glu Val Glu Leu Gly Lys Val Lys Ala Asp Ser
            20                  25                  30

Gly Ser Lys Thr Lys Ala Asp Ser Gly Gly Glu Thr Asp Ala Pro Ile
        35                  40                  45

Arg Lys Arg Phe Lys Leu Thr Pro Pro Gln Pro Thr Ile Met Pro Ile
    50                  55                  60

Ser Ile Ala Asp Arg Asp Phe Gly Val Asp Val Thr Asn Ile Pro Gln
65                  70                  75                  80

Ala Gln Val Gln Pro Pro Gln Gln Ala Asn Asp Pro Leu Val Arg Gly
                85                  90                  95

Val Arg Arg Ile Ala Trp Leu Lys Glu Cys Ala Gly Ile Asp Tyr Met
            100                 105                 110

Val Lys Asp Pro Asn Asn Pro Asn Gly Pro Met Met Ile Asn Pro Ile
        115                 120                 125

Leu Leu Asn Ile Pro Gln Gly Asn Pro Asn Ala Gln Gly Asn Pro Pro
    130                 135                 140

Gln Arg Ala Asn Pro Pro Ala Gly Phe Asn Ile His Asn His Glu Gln
145                 150                 155                 160

Trp Arg His Phe Val Val Gly Leu Ala Ala Leu Ser Asn Ala Asn Lys
                165                 170                 175

Pro Ser Ala Ser Pro Val Lys Val Leu Ser Asp Lys Ile Thr Gln Ile
            180                 185                 190

Tyr Ser Asp Ile Lys Pro Phe Asp Ile Ala Gly Ile Asp Val Pro
        195                 200                 205

Asp Thr Ser Leu Pro Asn Ser Ala Ser Val Glu Gln Ile Gln Asn Lys
    210                 215                 220

Met Gln Glu Leu Asn Asp Leu Leu Glu Glu Leu Arg Glu Ser Phe Asp
225                 230                 235                 240

Gly Tyr Leu Gly Gly Asn Ala Phe Ala Asn Gln Ile Gln Leu Asn Phe
                245                 250                 255

Val Met Pro Gln Gln Ala Gln Gln Gly Gln Gly Gln Gln Gln
            260                 265                 270

Ala Gln Ala Thr Ala Gln Glu Ala Val Ala Ala Ala Val Arg Leu
        275                 280                 285

Leu Asn Gly Asn Asp Gln Ile Ala Gln Leu Tyr Lys Asp Leu Val Lys
    290                 295                 300

Leu Gln Arg His Ala Gly Ile Lys Lys Ala Met Glu Lys Leu Ala Ala
305                 310                 315                 320
```

```
Gln Gln Glu Glu Asp Ala Lys Asn Gln Gly Glu Gly Asp Cys Lys Gln
                325                 330                 335

Gln Gln Gly Thr Ser Glu Lys Ser Lys Glu Gly Ser Lys Lys Glu Pro
            340                 345                 350

Glu Phe Asp Leu Ser Met Ile Val Gly Gln Val Lys Leu Tyr Ala Asp
        355                 360                 365

Val Met Ile Thr Glu Ser Val Ser Ile
        370                 375

<210> SEQ ID NO 3
<211> LENGTH: 377
<212> TYPE: PRT
<213> ORGANISM: Orientia tsutsugamushi
<220> FEATURE:
<221> NAME/KEY: MISC_FEATURE
<223> OTHER INFORMATION: Chimeric protein 3 based on sequences of
      recombinant r56 proteins from multiple stains

<400> SEQUENCE: 3

Met Thr Ile Thr Pro Ser Phe Arg Ala Glu Leu Gly Val Met Tyr Leu
1               5                   10                  15

Arg Asn Ile Thr Ala Gln Val Glu Glu Gly Lys Val Lys Ala Asp Ser
            20                  25                  30

Gly Ser Lys Thr Lys Ala Asp Ser Gly Gly Glu Thr Asp Ala Pro Ile
        35                  40                  45

Arg Lys Arg Phe Lys Leu Thr Pro Pro Gln Pro Thr Ile Met Pro Ile
50                  55                  60

Ser Ile Ala Asp Arg Asp Phe Gly Val Asp Val Pro Asn Ile Pro Gln
65                  70                  75                  80

Ala Gln Val Gln Pro Pro Gln Gln Ala Asn Asp Pro Leu Gln Arg Gly
                85                  90                  95

Val Arg Arg Ile Ala Trp Leu Lys Asn Cys Ala Gly Ile Asp Tyr Met
            100                 105                 110

Val Lys Asp Pro Asn Asp Pro Asn Gly Pro Met Met Ile Asn Pro Ile
        115                 120                 125

Leu Leu Asn Ile Pro Gln Gly Asn Pro Asn Ala Gln Gly Asn Pro Pro
    130                 135                 140

Gln Arg Ala Asn Pro Pro Ala Gly Phe Asn Ile His Asn His Glu Gln
145                 150                 155                 160

Trp Arg His Phe Val Val Gly Leu Ala Ala Leu Ser Asn Ala Asn Lys
                165                 170                 175

Pro Ser Ala Ser Pro Val Lys Val Leu Ser Asp Lys Ile Thr Gln Ile
            180                 185                 190

Tyr Ser Asp Ile Lys Pro Phe Ala Asp Ile Ala Gly Ile Asp Val Pro
        195                 200                 205

Asp Thr Ser Leu Pro Asn Ser Ala Ser Val Glu Gln Ile Gln Asn Lys
    210                 215                 220

Met Gln Glu Leu Asn Asp Leu Leu Glu Glu Leu Arg Glu Ser Phe Asp
225                 230                 235                 240

Gly Tyr Leu Gly Gly Asn Ala Phe Ala Asn Gln Ile Gln Leu Asn Phe
                245                 250                 255

Val Met Pro Gln Gln Ala Gln Gln Gly Gln Gly Gln Gln Gln Gln Gln
            260                 265                 270

Ala Gln Ala Thr Ala Gln Glu Ala Val Ala Ala Ala Val Arg Leu
        275                 280                 285

Leu Asn Gly Asn Asp Gln Ile Ala Gln Leu Tyr Lys Asp Leu Val Lys
    290                 295                 300
```

Leu Gln Arg His Ala Gly Ile Lys Lys Ala Met Glu Lys Leu Ala Ala
305                 310                 315                 320

Gln Gln Glu Glu Asp Ala Lys Asn Gln Gly Glu Gly Asp Cys Lys Gln
            325                 330                 335

Gln Gln Gly Thr Ser Glu Lys Ser Lys Lys Gly Lys Asp Lys Glu Ala
        340                 345                 350

Glu Phe Asp Leu Ser Met Ile Val Gly Gln Val Lys Leu Tyr Ala Asp
    355                 360                 365

Val Met Ile Thr Glu Ser Val Ser Ile
370                 375

<210> SEQ ID NO 4
<211> LENGTH: 370
<212> TYPE: PRT
<213> ORGANISM: Orientia tsutsugamushi
<220> FEATURE:
<221> NAME/KEY: MISC_FEATURE
<223> OTHER INFORMATION: TA763r56 Cloning sequence

<400> SEQUENCE: 4

Met Thr Ile Thr Pro Ser Ile Arg Ala Glu Leu Gly Val Met Tyr Leu
1               5                   10                  15

Arg Asn Ile Ser Ala Glu Val Glu Leu Gly Lys Val Lys Ala Asp Ser
            20                  25                  30

Gly Ser Lys Thr Lys Ala Asp Ser Gly Gly Glu Thr Asp Ala Pro Ile
        35                  40                  45

Arg Lys Arg Phe Lys Leu Thr Pro Pro Gln Pro Thr Ile Met Pro Ile
    50                  55                  60

Ser Ile Ala Asp Arg Asp Phe Gly Val Asp Val Thr Asn Ile Pro Gln
65                  70                  75                  80

Ala Gln Val Gln Pro Pro Gln Gln Ala Asn Asp Pro Leu Val Arg Gly
                85                  90                  95

Val Arg Arg Ile Ala Trp Leu Lys Glu Tyr Ala Gly Ile Asp Tyr Met
            100                 105                 110

Val Lys Asp Pro Asn Asn Pro Gly Arg Met Met Val Asn Pro Val Leu
        115                 120                 125

Leu Asn Ile Pro Gln Gly Pro Pro Ala Gln Asn Pro Arg Ala Ala Met
    130                 135                 140

Gln Pro Cys Asn Ile Leu Asp His Asp His Trp Lys His Phe Val Val
145                 150                 155                 160

Gly Val Thr Ala Leu Ser Asn Ala Asn Lys Pro Ser Ala Ser Pro Val
                165                 170                 175

Lys Ile Leu Ser Glu Lys Ile Thr Gln Ile Tyr Ser Ser Ile Arg Pro
            180                 185                 190

Phe Ala Asp Ile Ala Gly Ile Asp Val Pro Asp Ala Gly Leu Pro Asn
        195                 200                 205

Ser Ala Thr Val Glu Gln Ile Gln Asn Lys Met Gln Glu Leu Asn Asp
    210                 215                 220

Val Leu Glu Glu Leu Arg Glu Ser Phe Asp Gly Tyr Leu Gly Gly Asn
225                 230                 235                 240

Ala Phe Ala Asn Gln Ile Gln Leu Asn Phe Val Met Pro Gln Gln Ala
                245                 250                 255

Gln Gln Gln Gly Gln Gly Gln Gln Gln Ala Gln Ala Thr Ala Gln
            260                 265                 270

Glu Ala Val Ala Ala Ala Val Arg Leu Leu Asn Gly Asn Asp Gln
        275                 280                 285

-continued

```
Ile Ala Gln Leu Tyr Arg Asp Leu Val Lys Leu Gln Arg His Ala Gly
    290                 295                 300

Ile Lys Lys Ala Met Glu Lys Leu Ala Ala Gln Gln Glu Glu Asp Ala
305                 310                 315                 320

Lys Asn Gln Gly Glu Gly Asp Cys Lys Gln Gln Gly Thr Ser Glu
                325                 330                 335

Lys Ser Lys Glu Gly Ser Lys Lys Glu Pro Glu Phe Asp Leu Ser Met
                340                 345                 350

Ile Val Gly Gln Val Lys Leu Tyr Ala Asp Val Met Ile Thr Glu Ser
        355                 360                 365

Val Ser
    370

<210> SEQ ID NO 5
<211> LENGTH: 526
<212> TYPE: PRT
<213> ORGANISM: Orientia tsutsugamushi
<220> FEATURE:
<221> NAME

```
Phe Ala Asp Ile Ala Gly Ile Asp Val Pro Asp Ala Gly Leu Pro Asn
            275                 280                 285

Ser Ala Thr Val Glu Gln Ile Gln Asn Lys Met Gln Glu Leu Asn Asp
            290                 295                 300

Val Leu Glu Glu Leu Arg Glu Ser Phe Asp Gly Tyr Leu Gly Gly Asn
305                 310                 315                 320

Ala Phe Ala Asn Gln Ile Gln Leu Asn Phe Val Met Pro Gln Gln Ala
                325                 330                 335

Gln Gln Gln Gly Gln Gly Gln Gln Gln Gln Ala Gln Ala Thr Ala Gln
            340                 345                 350

Glu Ala Val Ala Ala Ala Val Arg Leu Leu Asn Gly Asn Asp Gln
            355                 360                 365

Ile Ala Gln Leu Tyr Arg Asp Leu Val Lys Leu Gln Arg His Ala Gly
            370                 375                 380

Ile Lys Lys Ala Met Glu Lys Leu Ala Ala Gln Gln Glu Glu Asp Ala
385                 390                 395                 400

Lys Asn Gln Gly Glu Gly Asp Cys Lys Gln Gln Gly Thr Ser Glu
                405                 410                 415

Lys Ser Lys Glu Gly Ser Lys Lys Glu Pro Glu Phe Asp Leu Ser Met
            420                 425                 430

Ile Val Gly Gln Val Lys Leu Tyr Ala Asp Val Met Ile Thr Glu Ser
            435                 440                 445

Val Ser Ile Tyr Ala Gly Val Gly Ala Gly Leu Ala Tyr Thr Ser Gly
            450                 455                 460

Lys Ile Asp Asp Lys Asp Thr Lys His Thr Gly Met Val Val Ser Gly
465                 470                 475                 480

Ala Leu Gly Val Ala Ile Asn Ala Ala Glu Gly Val Tyr Val Asp Ile
                485                 490                 495

Glu Gly Ser Tyr Met Tyr Ser Phe Ser Lys Ile Glu Glu Lys Tyr Ser
            500                 505                 510

Ile Asn Pro Leu Met Ala Ser Val Gly Val Arg Tyr Asn Phe
            515                 520                 525
```